United States Patent [19]

Menes

[11] Patent Number: 5,531,696
[45] Date of Patent: Jul. 2, 1996

[54] ELASTOMERIC DRIVER FOR EPIDURAL RESISTANCE SYRINGE

[76] Inventor: Cesar M. Menes, 12905 E. Wolverton, Cerritos, Calif. 90701

[21] Appl. No.: 166,213

[22] Filed: Dec. 13, 1993

[51] Int. Cl.⁶ .................................................. A61M 37/00
[52] U.S. Cl. ......................... 604/131; 604/208; 206/805
[58] Field of Search ..................................... 604/131, 208, 604/229, 132–135; 206/805

[56] References Cited

U.S. PATENT DOCUMENTS

| | | | |
|---|---|---|---|
| 1,797,539 | 3/1931 | Arthur | 206/805 |
| 4,636,197 | 1/1987 | Chu | 604/207 |
| 4,950,163 | 8/1990 | Zimble | 604/209 |
| 5,024,662 | 6/1991 | Menes et al. | 604/218 |

FOREIGN PATENT DOCUMENTS

0394334  6/1933  European Pat. Off. ............... 206/805

Primary Examiner—John D. Yasko
Assistant Examiner—Ronald Stright, Jr.
Attorney, Agent, or Firm—Natan Epstein

[57] ABSTRACT

A syringe, particularly for epidural anesthesia, has an elastomeric driver in the form of a single elastic band perforated for mounting onto the tip of the syringe between the barrel and the needle hub. The elastic band is stretched into engagement with the thumbrest of the plunger to drive the plunger to full depression into the syringe barrel. The elastic band extends symmetrically on either side of the barrel to apply balanced force. Various configurations for the elastic band are disclosed.

21 Claims, 1 Drawing Sheet

ELASTOMERIC DRIVER FOR EPIDURAL RESISTANCE SYRINGE

BACKGROUND OF THE INVENTION

1. Field of the Invention

The present invention pertains to the field of medical syringes and more particularly concerns elastomeric drivers for depressing the plunger of resistance syringes used for accurately positioning an epidural needle in preparation for injection of anesthetic into the epidural space of the spinal cord.

2. State of the Prior Art

Epidural anesthesia involves the injection of a liquid anesthetic substance into the epidural space which surrounds the dura mater which in turn surrounds the spinal cord proper. The epidural space is defined between the ligamentum flavum on the posterior or back side of the spinal cord, and the anterior longitudinal ligament on the anterior or frontal side of the spinal cord. These flexible but tough ligaments interconnect the bony vertebrae which enclose and protect the spinal cord and spinal canal.

A dose of an anesthetic such as lidocaine or bupivacaine, by way of example, produces a regional nerve block suitable for surgical procedures to be performed on portions of the anatomy affected by the nerve block, primarily but not limited to portions of the anatomy below the level of the spinal column at which the anesthetic is injected.

In the preferred midline technique the epidural needle passes through the supraspinous, interspinous and ligamentum flavum structures before entering the epidural space. Insertion of the needle into the epidural space is complicated by the lack of feedback as to the position of the needle tip, coupled with the imperative need to avoid puncturing the dura mater which surrounds the spinal cord, since there is potential for catastrophic trauma to the spinal cord with the epidural needle. Extreme caution must therefore be exercised in the positioning of the needle tip, which must pierce through the tough, resilient, leather-like ligamentum flavum and then stop immediately within the narrow epidural space, short of puncturing the dura mater.

The needle must be moved through the ligamentum flavum very slowly and in a carefully controlled fashion. At the same time, pressure is applied to the plunger of the attached syringe which is filled either with air or saline solution. The object is to continuously test for loss of resistance to injection, experienced when the needle lumen enters the epidural space after clearing the ligamentum flavum. This loss of resistance is experienced by little if any resistance to injected air or fluid, and a negative aspiration test then indicates that the needle lumen is properly positioned in the epidural space. Special syringes, known as loss of resistance syringes and characterized by very low friction between the plunger and the barrel of the syringe, are used for positioning the needle lumen in the epidural space. Once correct positioning of the needle is achieved, the resistance syringe is separated from the epidural needle and another syringe, loaded with the anesthetic is attached, after which the anesthetic is injected.

In order to appreciate the contribution being made by the present invention, it is important to understand the demands placed upon the anesthesiologist's dexterity by this procedure. It is of critical importance that the needle traverse the ligamentum flavum in a carefully measured and controlled manner. Typically, this is achieved by applying resistance to the advancing needle with the anesthesiologist's non-dominant hand (the left-hand if the anesthesiologist is right-handed) while the dominant hand applies pressure to the plunger of the resistance syringe to test for resistance to injection while at the same time slowly advances the needle. Variations of this technique may be adopted according to personal preference, for example the needle may be advanced continuously while pressure on the syringe barrel is also maintained continuously to test for resistance. In the alternative, the needle is advanced in very small increments, e.g. 1 millimeter, testing for resistance to injection after each advance.

The difficulty of correctly positioning the needle lumen in the epidural space has spurred many attempts to develop methods and devices for detecting and indicating correct needle placement. These expedients have generally exploited the low resistance to injection and subatmospheric pressure characteristic of the epidural space. One such technique involves placement of a drop of saline solution on the open hub of a epidural needle. The drop will be "sucked-in" as the needle lumen enters the epidural space where, for reasons not well understood, prevails sub-atmospheric pressure. Other means used for this purpose include capillary attachments with fluid indicators developed by Odom, or inflated balloons by Macintosh, which deflate upon entering the epidural space. It is also known to use spring loading devices to facilitate the loss of resistance phenomena which occur as the epidural needle passes from the dense ligamentum flavum into the lesser resistance of the epidural space.

U.S. Pat. No. 5,024,662, in which this applicant is a co-inventor, describes an attachment for a resistance syringe for aiding the anesthesiologist in correct placement of the epidural needle. The patented attachment has an elastomeric band retained to the syringe barrel by a ring which slides onto the syringe barrel against the finger flange of the syringe to anchor the ends of the elastic band to the barrel while a midportion of the band is pulled by the plunger of the syringe. Consequently, the plunger is urged by elastic force into the syringe barrel, but is held back by fluid, air or liquid in the barrel, until the needle lumen enters the epidural space. At that point the contents of the syringe are injected into the epidural space under the force of the stretched band, providing the anesthesiologist with immediate kinesthetic indication of correct needle placement.

While this arrangement works well, disposable elastomeric drivers have been developed by this applicant which are of still greater simplicity and very low cost.

SUMMARY OF THE INVENTION

The elastomeric drivers of this invention, described below in several alternative forms, are for use with a syringe of the type which has a syringe barrel, a tip at one end of the barrel to which can be mounted the hub of an epidural needle, a plunger which makes a sliding fit into the opposite end of the barrel, and a thumbrest at an exterior end of the plunger.

In general, the elastomeric driver of this invention in its various forms has a first portion which is engageable to the tip of the syringe barrel and a second portion engageable to the thumbrest of the plunger. In each embodiment the elastomeric driver has a width dimension and a thickness dimension. The elastomeric driver is apertured for admitting the tip of the syringe barrel. The aperture is in the form of one or more holes. Each such hole passes through the thickness dimension and is positioned within the width dimension of the driver. As installed on the syringe, the length of the elastomeric driver is such as to normally urge the plunger to full depression into the barrel. That is, the effective installed length of the elastomeric driver is smaller than the distance between the barrel tip and the plunger thumbrest with the plunger fully depressed into the barrel, and the elastomeric driver remains somewhat stretched between the tip and thumbrest with the plunger fully depressed in the barrel.

More specifically, the elastomeric driver according to this invention may take several distinct forms.

In a first, closed loop variant of the invention, the elastomeric driver is a continuous elastic band in which the first and second portions, engageable respectively to the barrel tip and the thumbrest, are at diametrically opposed points of the band. The band may be an annular flat band of elastic material and of uniform width. The first portion of the elastomeric driver may be a portion of the band adjacent to a single small hole in the band. The perforated portion of the band is fitted onto the syringe tip and the diametrically opposite portion of the band is stretched over the thumbrest. The band may have two diametrically opposite holes, either of which can receive the barrel tip, so that the elastomeric band can be reversibly installed on the syringe. One or both of the first and second portions of the band may be enlarged in width, for example in the form of circular pads with a hole centered in the pad, for easier handling during installation and greater frictional contact with the thumbrest. One or both of the pads may be coated with adhesive for positive retention to the thumbrest.

In a second, open-ended variant of the invention, the elastomeric driver is a unitary band of elastic material with two opposite ends, each end being perforated for receiving the barrel tip. The elastomeric driver is installed on the syringe by sliding the two perforated ends one over the other onto the barrel tip, and then stretching a midportion of the elastomeric driver over the thumbrest of the plunger, for urging the plunger into the barrel under elastic tension of the elastic band. The two ends of the band are retained to the syringe tip between the hub of the epidural needle and the syringe barrel. The elastic band may be of uniform width with a small hole near each end. Alternatively, the ends of the band may be enlarged in the form of circular pads perforated by a small hole in the center of each end pad. The midportion of the band may be enlarged in width, for example, to form a circular pad midway between the ends of the band, for improved frictional contact with and retention to the thumbrest of the syringe. The midportion of the elastomeric driver, whether enlarged or not, may have an adhesive for positive retention of the midportion to the thumbrest.

In any of the various forms of the elastomeric driver, the elastic band may have a tab integral with the band and extending transversely therefrom adjacent to the thumbrest engaging portion of the band. The tab provides a convenient finger hold to facilitate handling and stretching of the band during installation on the syringe, after the perforated portion of the band has been engaged to the tip.

It is preferred that the elastic material of the elastomeric driver provide sufficient elastic tension for positively driving the plunger into the barrel as soon as the needle lumen is unoccluded upon entry into the epidural space, but without excessive impact of the plunger against the tip end of the barrel. In particular, the elastic force applied by the elastomeric driver should be such as to avoid shattering the syringe when used with a glass syringe, yet provide positive kinesthetic indication of entry into the epidural space.

These and other features, improvements and advantages of the present invention will be better understood by reference to the following detailed description of the preferred embodiments and the accompanying drawings.

DETAILED DESCRIPTION OF THE PREFERRED EMBODIMENTS

Figure 1:
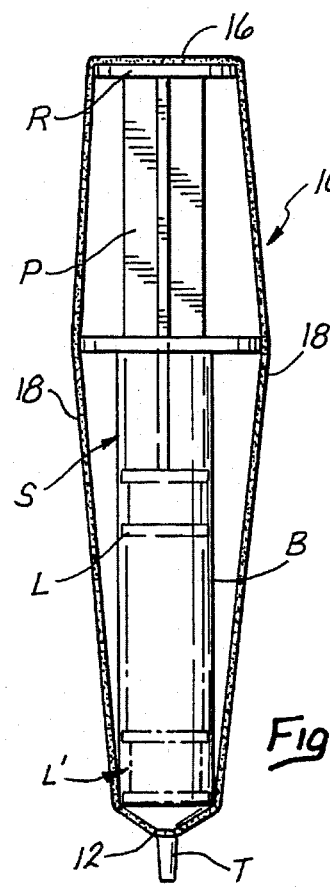
FIG. 1 is a side view of a typical disposable resistance syringe fitted with an elastomeric driver according to this invention.
Figure 1A:
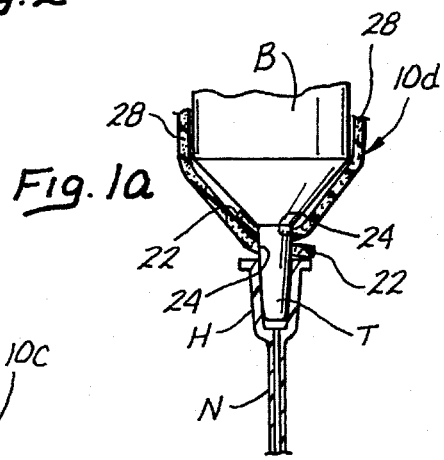
FIG. 1a is a detail view partly in section showing the end-over-end attachment of the elastic band to the syringe tip between the needle hub and the syringe barrel.

FIG. 1 shows a typical disposable plastic resistance syringe generally designated by the letter S and which has a cylindrical hollow syringe barrel B with a tip T at one end. The tip T has an axial bore opening into the interior of barrel B, as shown in FIG. 1a, where the hub H of an epidural needle N is shown mounted onto the tip T to place the hollow needle in fluidic communication with the interior of the barrel B. A syringe plunger P makes a sliding seal L inside the barrel B and is movable from the drawn condition shown in solid lining in FIG. 1 to a depressed condition L' shown in phantom lining. The plunger has a thumbrest R at its exterior, free end.

FIG. 1 shows an elastomeric driver, generally designated by the numeral 10, installed on the syringe S. The elastomeric driver is a unitary elastomeric element which has a tip engaging portion 12 and a thumbrest engaging portion 16, the connecting portions 18 of the elastomeric element 10 being stretched between the barrel tip T and thumbrest R so as to urge the plunger P into the barrel B, from the solid-lined, drawn position of the plunger to the phantom lined, depressed position in FIG. 1.

Figure 2:
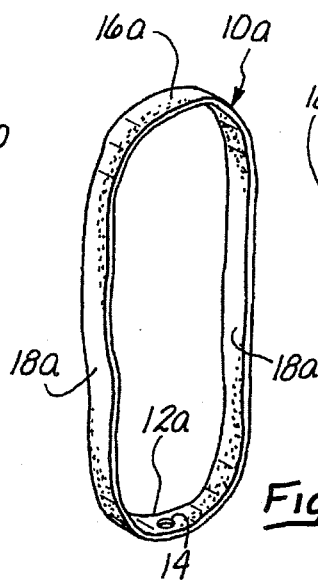
FIG. 2 is a perspective view of a first form of the elastomeric driver of this invention in the form of a continuous elastic band with a single hole.
Figure 3:
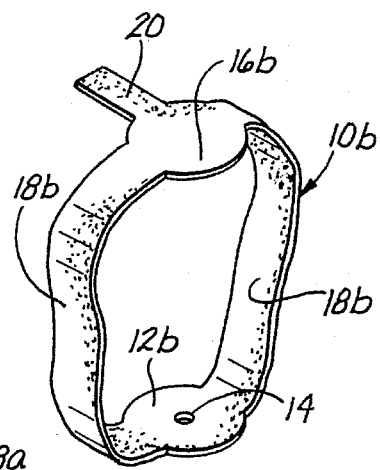
FIG. 3 is a perspective view of the elastomeric driver of this invention in the form of a continuous band with two diametrically opposed circular pad enlargements, one enlargement being perforated for mounting to the barrel tip, the other enlargement having a tab for easier handling in stretching the band over the thumbrest of the syringe.
Figure 4:
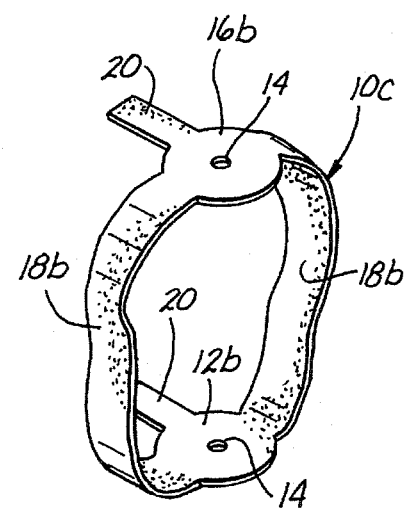
FIG. 4 is a perspective view of a third form of the elastomeric driver of this invention in the form of a continuous band having two diametrically opposed circular pad enlargements, each enlargement being perforated and provided with a tab for easier fitting of the band to a syringe.

The elastomeric driver 10 can take different forms, five of which are illustrated in FIGS. 2 through 6. The embodiments illustrated in FIGS. 2, 3 and 4 are characterized in that the elastomeric element is a continuous band of elastic material. The embodiments of FIGS. 5 and 6 on the other hand are open-ended bands of elastic material, i.e, which have two opposite ends. All of the illustrated embodiments, however, can be installed on the syringe S in the manner illustrated in FIG. 1, as will now be described.

The elastomeric driver 10a of FIG. 2 is a continuous elastic band of uniform width with a small hole 14 which is of sufficient size to admit the barrel tip T of the syringe S. The hole 14 may be slightly undersized with respect to the diameter of the tip T, so that the tip engaging portion 12a of the elastic band 10a is press-fitted onto the syringe tip T. The diametrically opposite thumbrest engaging portion 16a of the band 10a is stretched over and diametrically across the thumbrest R of the syringe S. The length of the band 10a is such that the connecting portions 18a are elastically stretched between the thumbrest R and the barrel tip T even with the plunger T in the fully depressed condition suggested at L' in FIG. 1.

The embodiment of FIG. 3 is a continuous band 10b of elastic material which is wider along the connecting portions 18b than the width of the band 10a in FIG. 2. The band 10b has a hole 14 sized to receive the syringe tip T, and is enlarged in width to form a circular pad 12b around the hole 14 which receives the barrel tip T. A second circular pad 16b is the thumbrest engaging portion of the elastomeric driver 10b and is situated diametrically opposite to the tip engaging pad 12b along the closed band 10b, i.e., the two pads 16a and 16b are connected by two portions 18b of equal length. A tab 20 extends from the thumbrest engaging pad 16b transversely to the band 10b, and serves as a convenient finger hold when stretching the band 10b away from the syringe tip T in order to engage the pad 16b to the thumbrest R after fitting the pad 12b onto the syringe tip T.

The embodiment 10c of FIG. 4 differs from that of FIG. 3 only in that the circular pad 16b also has a center hole 14, and pad 12b has a tab 20 similar to the top 20 of pad 16b in FIG. 3. The elastomeric driver 10c of FIG. 4 is consequently reversible in that either pad 12b, 16b may be fitted to the syringe tip T as the tip engaging portion of the elastomeric driver, the other of the pads 16b and 12b being engageable to the thumbrest R by stretching the connecting portions 18b as shown in FIG. 1.

Figure 5:
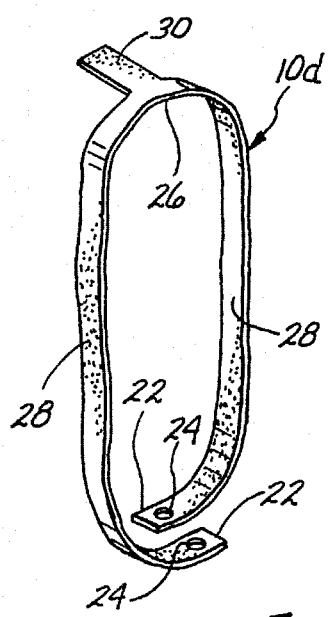
FIG. 5 is a fourth form of the elastomeric driver of this invention in the form of an elastic band having two perforated opposite ends and a transverse tab at a midportion of the band.

The embodiment of FIG. 5 is an open ended band of uniform width in which the tip engaging portion of the elastomeric driver 10c includes two opposite ends 22, each end being perforated with a hole 24 sized to receive the syringe tip T. The ends 22 of the band 10d are fitted onto the syringe tip one over the other as shown in FIG. 1a, stacked one over the other along the length of tip T. The thumbrest engaging portion of the band 10d is a midportion 26 of the band equidistant between the band ends 22. The midportion 26 is frictionally engaged to the thumbrest R by stretching the connecting portions 28 of the band along diametrically opposed sides of the syringe S, analogously to the portions 18 in FIG. 1, so that the midportion 26 lies diametrically across the thumbrest R, similarly to portion 16 in FIG. 1. Installation of the elastomeric driver 10d and engagement to the syringe thumbrest R is facilitated by a tab 30 integral to the band 10d which extends transversely to the midportion 26 as seen in FIG. 5. The ends 22 are secured to the tip T because the two ends 22 are held under elastic tension transversely to the length of the tip T by the stretched connecting portions 28 of the band. The tension of the portions 28 keeps the two ends 22 against the end of the syringe barrel B so that installation of the elastomeric driver 10d does not interfere with mounting of the needle hub H on the tip T.

Figure 6:
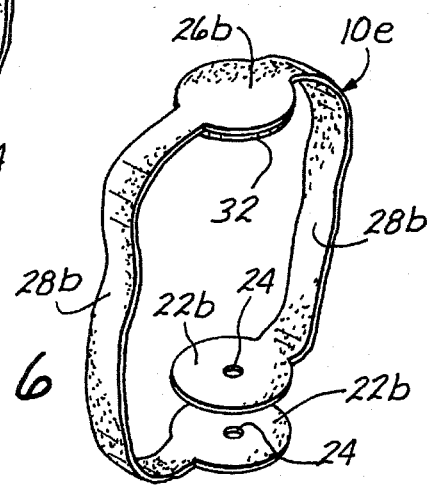
FIG. 6 is a fifth form of the elastomeric driver of this invention in the form of a flat elastic band having two opposite ends enlarged to form circular pads each perforated by a center hole, and a midportion of the band enlarged to form a circular pad for improved contact with the thumbrest.

The embodiment 10e shown in FIG. 6 differs from the elastomeric driver 10d of FIG. 5 in that the band 10e is somewhat wider along connecting portions 28d than band 10d, the tip engaging ends have been enlarged to form circular end pads with the tip receiving hole 24 centered in each end pad 22b, and the thumbrest engaging midportion 26b is of enlarged width to form a circular pad integral with the band 10e and equidistant to the end pads 22b. The elastomeric driver 10e is fitted to the syringe S by pressing the two ends 22b onto the syringe tip T, so that the tip passes consecutively through the hole 24 in each pad 22b, and the end pads 22b are stacked one over the other on the tip T as just explained in connection with the band 10d in FIG. 1a. The connecting portions 28b are then stretched by pulling on the midportion 26b over and onto the thumbrest R where it is retained by frictional engagement under the elastic tension of the stretched portions 28b extending on either side of the syringe S, as shown for the side portions 18 in FIG. 1.

The enlarged width of the elastic band about the holes 14, 24 in the several embodiments described above substantially reinforces the strength of the material surrounding the holes and ensures against tearing of the material during installation of the elastomeric driver to the syringe S, as might occur by possible mishandling of the elastomeric driver, such as excessive stretching of the elastic band. The enlarged midportion of the elastomeric driver, as at 16b in FIG. 3, and 26b in FIG. 6, provides a substantially increased area of contact and a consequent increase in frictional engagement between the band midportion and the thumbrest R, better ensuring retention of the elastomeric driver while handling the syringe S. The enlarged midportions 16b and 26b may also be somewhat easier to grasp and handle by some users during installation of the elastomeric driver onto the resistance syringe S. Positive retention of the band midportion to the thumbrest R can be ensured by providing a layer 32 of adhesive material on an inner surface of the elastomeric driver which makes contact with the thumbrest R, as shown by way of example for the elastomeric driver 10e in FIG. 6. This adhesive may be a suitable pressure activated adhesive, and may be initially covered with a release sheet which is removed just prior to installation of the elastomeric driver onto the resistance syringe S. The use of adhesive in this fashion is appropriate for any of the embodiments shown in FIGS. 2 through 6.

Installation of the elastomeric driver on the resistance syringe S, in any of the described embodiments, does not interfere in any way with the normal functioning of the syringe. The epidural needle hub H fits onto the syringe tip T in the normal manner, as illustrated in FIG. 1a. The tip engaging portion or portions of the elastomeric driver fit onto the tip T between the needle hub H and the bottom end of the syringe barrel B, without prejudice to normal mounting of the epidural needle to the syringe. The needle hub H also acts as a stop for the tip engaging portion or portions of the elastomeric driver, which can be beneficial in the occasional case where the elastomeric driver 10 might slip off of the thumbrest R, in which case the needle hub may help retain the elastomeric driver to the syringe S.

The elastomeric drivers 10a through 10e are unitary elastomeric elements which can be produced in large quantities from thin elastic sheet material or thin walled elastic tubing, by dye cutting or other well known methods. The choice of a particular elastomeric material is not critical and may be selected from among the numerous commonly available elastic materials, including those employed in the manufacture of ordinary commercially available rubber bands of the type sold in office supplies stores and the like. The thickness of the elastic material and the width of the elastic band is selected so as to provide a positive elastic force driving the syringe plunger P into the syringe barrel B when there is no resistance to fluid flow through the epidural needle N, thereby to provide a positive kinesthetic indication to the anesthesiologist of proper needle placement in the epidural space. This general criterion allows a wide and non-critical choice of elastomeric band parameters including band dimensions and material. A suitable material for the elastomeric drivers in any of the embodiments described above is SBR natural rubber in 0.040 inch thickness for use with plastic disposable resistance syringes. The open-ended elastic band 10d may be 6 inches between the end holes 24. The continuous bands 10a, 10b and 10c ay be about 3 to 3.5 inches in flattened diameter, i.e. approximately 6 to 7 inches in circumference. SBR natural rubber in 0.010 inch thickness may be used with glass resistance syringes, in which case the length of the elastomeric drivers may be about 1 inch shorter than for the 0.040 thickness to partly adjust for the lower elastic strength of the thin band. However, many different elastic materials may be found suitable for making the elastomeric drivers of this invention, with proper adjustment of band thickness and length in accordance with the inherent elastic strength of the particular material, as will be evident to those having ordinary skill with such materials.

While certain preferred embodiments of the invention have been described and illustrated for purposes of clarity and example, it must be understood that many changes, substitutions, and modifications to the described embodiments will become obvious to those possessed of ordinary skill in the art without their thereby departing from the scope and spirit of the present invention which is defined by the following claims.

What is claimed is:

1. A syringe with elastomeric driver comprising:
   a syringe having a barrel, a tip for mounting a hypodermic needle to one end of said barrel, a plunger movable into an opposite end of the barrel, and a thumb rest at a free end of said plunger; and
   a unitary elastomeric band having opposite ends and a midportion, said ends being perforated for being fitted onto said tip between said hypodermic needle and said barrel, said midportion being engaged to said thumb rest for urging said plunger into said barrel, further comprising adhesive on said midportion for retaining the midportion to said thumb rest, said elastomeric band having a length between said ends and said midportion so as to urge said plunger to full depression into said barrel.

2. The syringe with elastomeric driver of claim 1 wherein said elastomeric element is a continuous band and said first and second means are at diametrically opposed points of said band.

3. The syringe with elastomeric driver of claim 2 wherein one or both of said first means and said second means are perforated for receiving said tip.

4. The syringe with elastomeric driver of claim 2 wherein at least one of said first means and said second means are portions of said band of enlarged width.

5. The syringe with elastomeric driver of claim 1 wherein said length is smaller than the distance between said tip and said thumb rest with said plunger fully depressed into said barrel.

6. The syringe with elastomeric driver of claim 1 wherein said elastomer element is stretched between said tip and said thumb rest with said plunger fully depressed in said barrel.

7. The syringe with elastomeric driver of claim 1 further comprising one or more tabs integral with said elastomeric element and extending laterally therefrom for facilitating manual attachment of the elastomeric element to said syringe.

8. The syringe with elastomeric driver of claim 1 wherein said band is flat and said ends are enlarged about said perforations.

9. The syringe with elastomeric driver of claim 1 wherein said ends are circular pads perforated in the middle.

10. The syringe with elastomeric driver of claim 1 wherein said midportion is of enlarged width for improved contact with said thumb rest.

11. The syringe with elastomeric driver of claim 1 wherein said elastomeric element includes diametrically opposed elastic portions along said barrel connecting said first means with said second means.

12. A syringe with elastomeric driver comprising:
    a syringe having a barrel, a tip for mounting a hypodermic needle to one end of said barrel, a plunger movable into an opposite end of the barrel, and a thumb rest at a free end of said plunger; and
    a continuous elastic band having a thickness dimension and a width dimension and two holes through said thickness dimension and within said width dimension at diametrically opposed locations along said band, said tip being inserted in one of said holes for retaining said band on said tip between said hypodermic needle and said barrel, a midportion of said band diametrically opposite to said one of said holes being engaged to said thumb rest for urging said plunger into said barrel.

13. The syringe with elastomeric driver of claim 12 wherein said band has two diametrically opposed pads of enlarged width, said two holes being each in one of said pads.

14. The syringe with elastomeric driver of claim 13 further comprising tab means integral with said band and extending transversely to said band from one or both of said pads as a hold for facilitating manual mounting or removal of said band on the syringe.

15. The syringe with elastomeric driver of claim 12 wherein said band is of enlarged width around said one of said holes.

16. The syringe with elastomeric driver of claim 12 further comprising a tab integral with said band and extending transversely therefrom and aligned with said one of said holes for facilitating mounting of the band to said tip.

17. The syringe with elastomeric driver of claim 12 further comprising a tab integral with said band and extending transversely therefrom at said midportion for facilitating engagement of said midportion to said thumb rest.

18. A syringe with elastomeric driver comprising:
    a syringe having a barrel, a tip for mounting a hypodermic needle to one end of said barrel, a plunger movable into an opposite end of the barrel, and a thumb rest at a free end of said plunger; and
    an elastic band having opposite ends and a midportion between said ends, said band having a thickness dimension and a width dimension, a hole in said band through said thickness dimension and within said width dimension near each of said ends, said tip being inserted through said hole in each of said ends for retaining both ends one over the other onto said tip between said hypodermic needle and said barrel, said midportion being adapted for stretching into engagement with said thumb rest for urging said plunger into said barrel, said midportion further being of enlarged width for improved frictional contact with said thumb rest.

19. The syringe with elastomeric driver of claim 18 wherein said band is flat and said ends are enlarged about said perforations.

20. The syringe with elastomeric driver of claim 18 wherein said ends are circular pads perforated in the center.

21. The syringe with elastomeric driver of claim 18 further comprising adhesive on said midportion for positive retention of the midportion to said thumb rest.

* * * * *